(12) United States Patent
Eidenschink

(10) Patent No.: US 7,294,124 B2
(45) Date of Patent: Nov. 13, 2007

(54) HYPOTUBE WITH IMPROVED STRAIN RELIEF

(75) Inventor: Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 8 days.

(21) Appl. No.: 10/034,448

(22) Filed: Dec. 28, 2001

(65) Prior Publication Data

US 2003/0125709 A1 Jul. 3, 2003

(51) Int. Cl.
*A61M 25/00* (2006.01)
(52) U.S. Cl. .............. 604/525; 604/96.01; 604/103.04; 604/103.09
(58) Field of Classification Search ........ 604/523–526, 604/103–10.09, 96.01; 607/122; 606/194–192
See application file for complete search history.

(56) References Cited

U.S. PATENT DOCUMENTS

| | | | |
|---|---|---|---|
| 4,762,129 A | 8/1988 | Bonzel | |
| 4,917,666 A * | 4/1990 | Solar et al. | 604/95.01 |
| 4,998,923 A * | 3/1991 | Samson et al. | 606/194 |
| 4,762,129 A | 7/1991 | Bonzel | |
| 5,040,548 A | 8/1991 | Yock | |
| 5,095,915 A * | 3/1992 | Engelson | 600/585 |
| 5,156,594 A | 10/1992 | Keith | |
| 5,322,505 A * | 6/1994 | Krause et al. | 604/24 |
| 5,387,193 A * | 2/1995 | Miraki | 604/102.02 |
| 5,458,613 A * | 10/1995 | Gharibadeh et al. | 606/194 |
| 5,477,856 A * | 12/1995 | Lundquist | 600/373 |
| 5,480,382 A | 1/1996 | Hammerslag et al. | |
| 5,496,294 A | 3/1996 | Hergenrother et al. | |
| 5,507,751 A * | 4/1996 | Goode et al. | 606/108 |
| 5,542,434 A | 8/1996 | Imran et al. | |
| 5,626,593 A | 5/1997 | Imran | |
| 5,658,251 A | 8/1997 | Ressemann et al. | |
| 5,743,876 A * | 4/1998 | Swanson | 604/96.01 |
| 5,810,867 A | 9/1998 | Zarbatany et al. | |
| 5,876,375 A | 3/1999 | Penny | |
| 5,911,715 A | 6/1999 | Berg et al. | |
| 5,957,903 A | 9/1999 | Mirzaee et al. | |
| 5,980,484 A | 11/1999 | Ressemann et al. | |
| 5,980,486 A | 11/1999 | Enger | |
| 6,013,069 A * | 1/2000 | Sirhan et al. | 604/96.01 |

(Continued)

FOREIGN PATENT DOCUMENTS

EP   1084728 A1   3/2001

(Continued)

OTHER PUBLICATIONS

International Search Report dated Jun. 17, 2003 (5 pages).

*Primary Examiner*—Kevin C. Sirmons
*Assistant Examiner*—Andrew Gilbert
(74) *Attorney, Agent, or Firm*—Crompton, Seager & Tufte LLC

(57) ABSTRACT

A hypotube for an intravenous catheter device is disclosed which includes a tubular shaft having a tubular wall defining a lumen. The shaft includes a main section integrally connected to a distal section. The distal section includes a first section connected to the second section and disposed between the second section and the main section. The second section includes an elongated stinger.

16 Claims, 3 Drawing Sheets

U.S. PATENT DOCUMENTS

| | | |
|---|---|---|
| 6,022,343 A | 2/2000 | Johnson et al. |
| 6,030,405 A | 2/2000 | Zarbatany et al. |
| 6,039,699 A | 3/2000 | Viera |
| 6,048,338 A | 4/2000 | Larson et al. |
| 6,066,114 A * | 5/2000 | Goodin et al. ......... 604/103.04 |
| 6,066,144 A * | 5/2000 | Wolf et al. ................. 606/139 |
| 6,102,890 A * | 8/2000 | Stivland et al. .......... 604/96.01 |
| 6,152,909 A * | 11/2000 | Bagaoisan et al. .......... 604/523 |
| 6,246,914 B1 * | 6/2001 | de la Rama et al. ........ 607/122 |
| 6,524,300 B2 * | 2/2003 | Meglin ....................... 604/523 |
| 6,533,754 B1 * | 3/2003 | Hisamatsu et al. ...... 604/96.01 |
| 6,575,958 B1 * | 6/2003 | Happ et al. ................. 604/525 |
| 6,579,246 B2 * | 6/2003 | Jacobsen et al. ............ 600/585 |
| 6,592,569 B2 * | 7/2003 | Bigus et al. ................ 604/523 |
| 6,623,448 B2 * | 9/2003 | Slater ...................... 604/95.01 |
| 2001/0029362 A1 | 10/2001 | Sirhan et al. |
| 2001/0037085 A1 | 11/2001 | Keith et al. |
| 2004/0059292 A1 | 3/2004 | Hisamatsu et al. |
| 2004/0249436 A1 * | 12/2004 | Aznoian et al. ............ 623/1.15 |
| 2006/0142696 A1 * | 6/2006 | Kumoyama et al. ... 604/103.04 |

FOREIGN PATENT DOCUMENTS

| | | |
|---|---|---|
| JP | 2001-095924 | * 10/2001 |
| WO | WO 2004/047899 | 6/2004 |

* cited by examiner

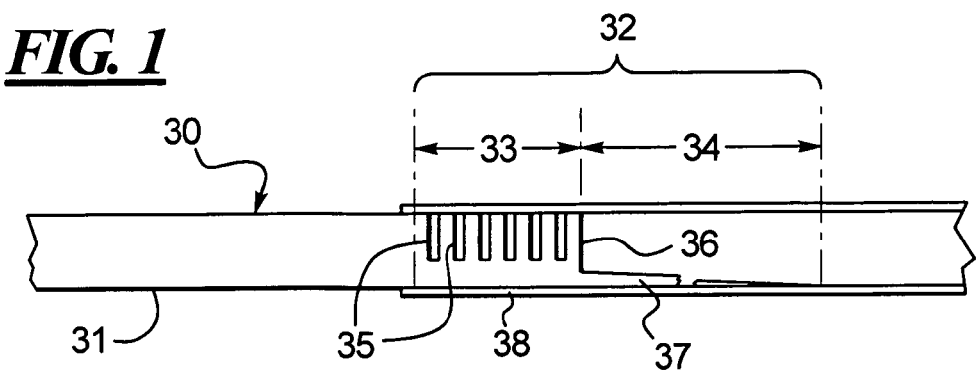
*FIG. 1*
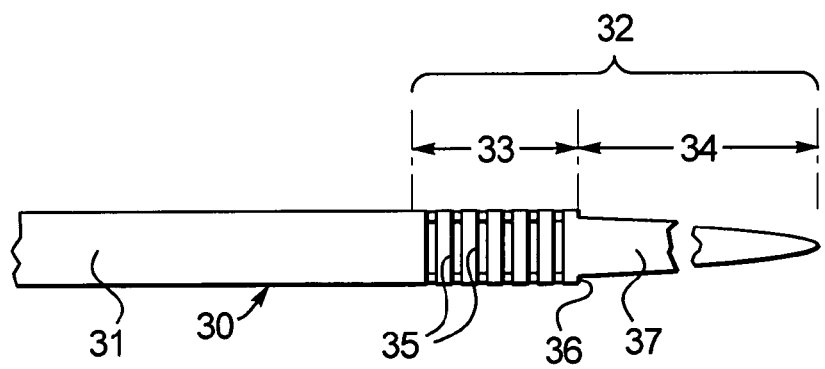
*FIG. 2*
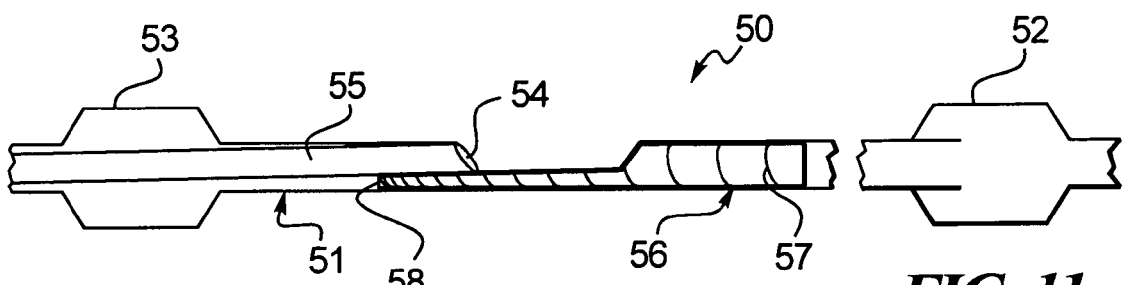
*FIG. 11*
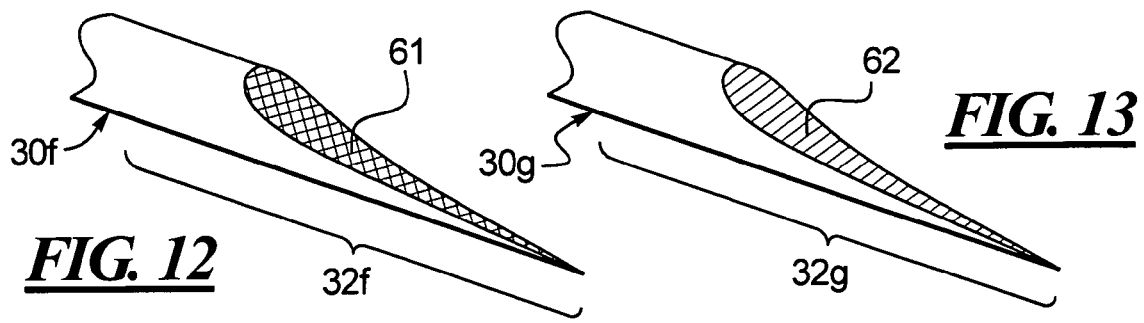
*FIG. 12*   *FIG. 13*

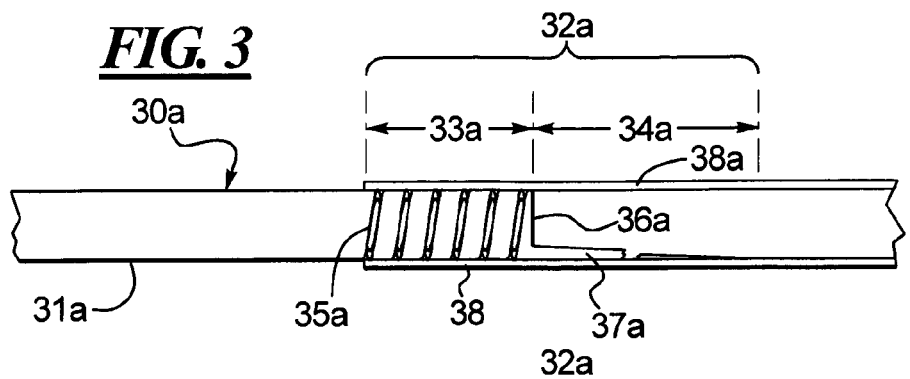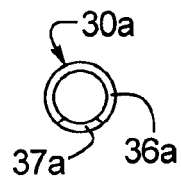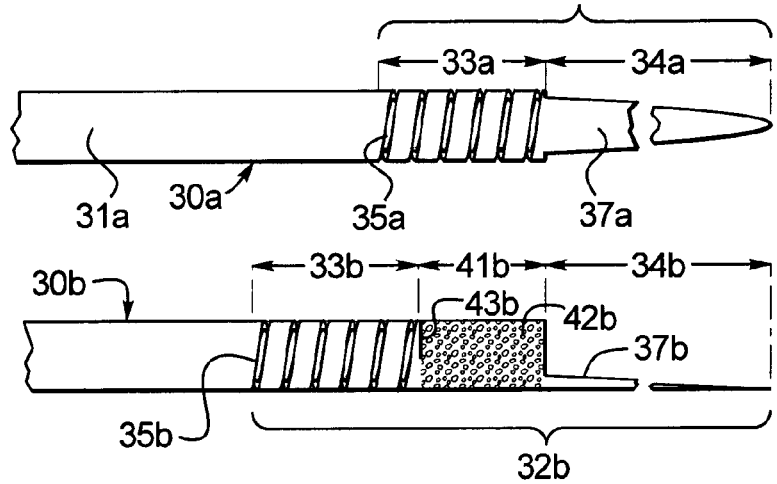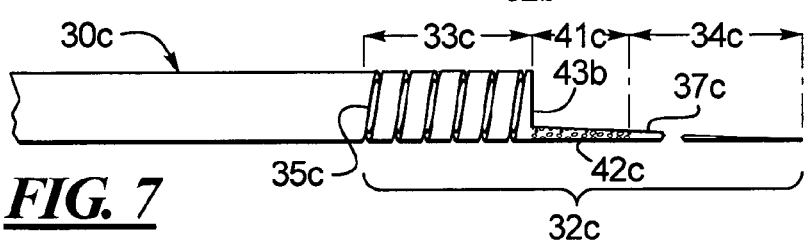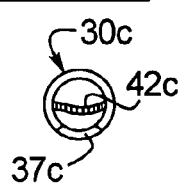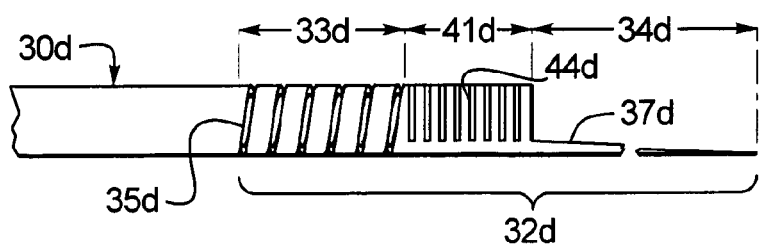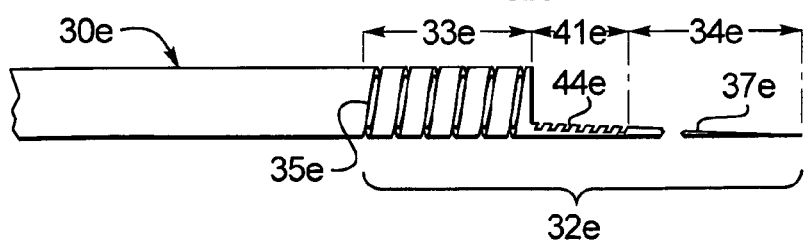

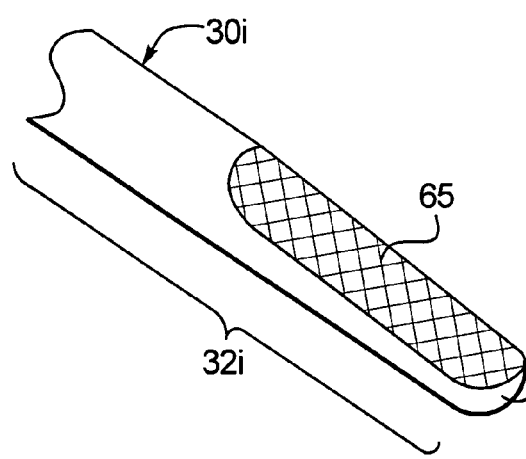
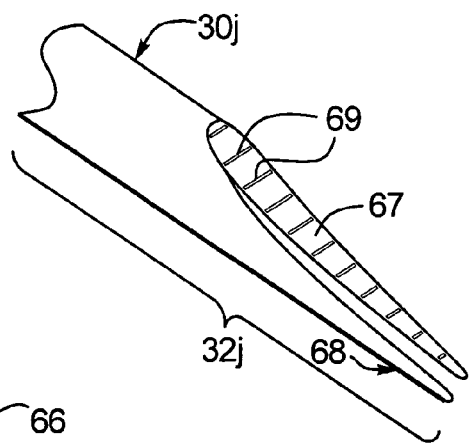
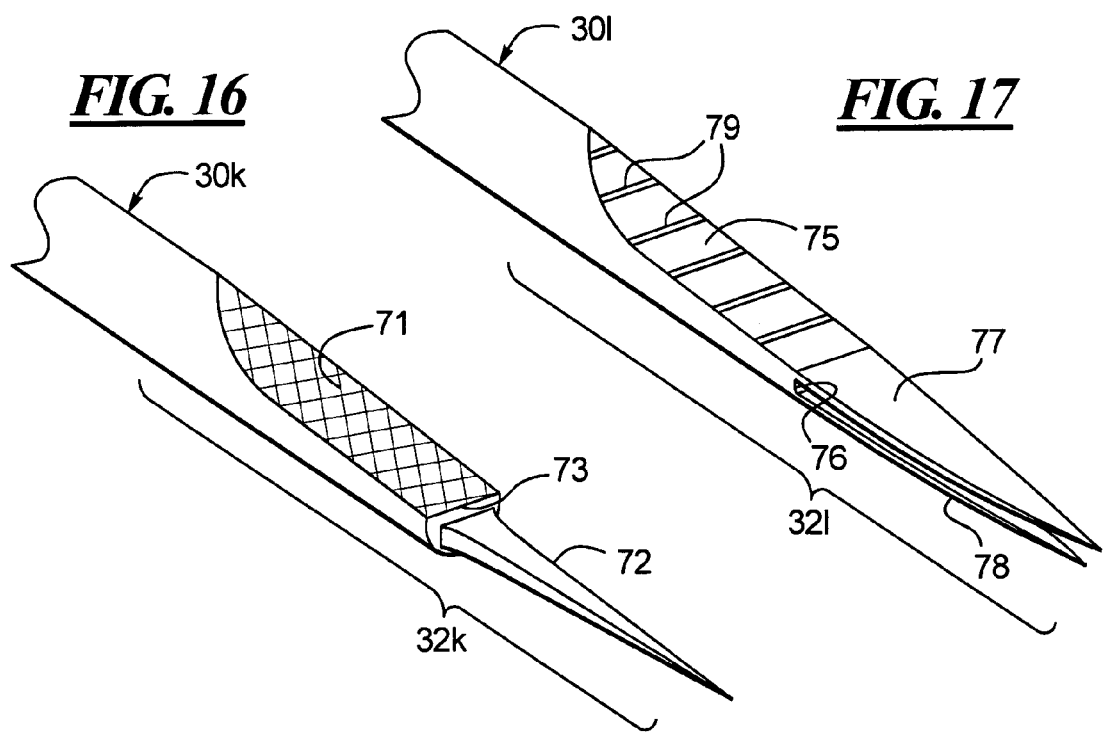

HYPOTUBE WITH IMPROVED STRAIN RELIEF

BACKGROUND

1. Technical Field

An improved hypotube for an intravascular catheter is disclosed. More specifically, an improved hypotube for use with a catheter is disclosed that provides improved strain relief or transitioning stiffness characteristics between a distal end of the hypotube and a proximal end of the catheter.

2. Description of the Related Art

Intravascular catheters are widely used for a variety of diagnostic and therapeutic purposes. Specifically, angioplasty has been developed as an alternative to bypass surgery for treating vascular diseases or other conditions that occlude or reduce blood flow in a patient's vascular system. Balloon angioplasty has proven to be a useful and often a preferred treatment for coronary diseases that cause blockages, also known as stenosis, in coronary arteries as well as other parts of the vascular system.

One current angioplasty technique makes use of a single operator exchange or rapid exchange catheter assembly as illustrated in U.S. Pat. No. 5,156,594. The catheter assembly shown therein includes a balloon catheter having a proximal end including a hypotube. A distal end of the balloon catheter is connected to a balloon. The balloon catheter includes a main lumen that is in communication with the lumen of the hypotube as well as a relatively short separate lumen which accommodates a guidewire. In practice, the guidewire is inserted into the patient's vascular system through a guide catheter. The balloon catheter assembly is then fed through the guide catheter and over the guidewire. The guidewire is fed through the distal end of the guidewire lumen and out the proximal end of the guidewire lumen which is disposed proximal of the balloon. In contrast to an over-the-wire catheter system, if the catheter needs to be changed, the position of the guidewire can be maintained by withdrawing the catheter without the need for a long guidewire or an extension wire.

Advancing the catheter assembly to position the balloon across a stenosis can be a difficult and time consuming task due to the narrow and tortuous passages through which the catheter assembly must be passed. The balloon must be positioned precisely and movement of the balloon through the vascular system must be conducted in as atraumatic manner as possible.

To be effective, the catheter assembly preferably has two distinct features. First, the catheter assembly must have sufficient "pushability" or axial strength thereby enabling a longitudinal force to be transmitted through the assembly so that the physician can push the catheter assembly through the vascular system to the stenosis. Concurrently, the catheter assembly preferably may also be sufficiently flexible so that the catheter assembly has good "trackability" so as to enable the physician to navigate the tortuous passages of the patient's vascular system.

To satisfy these criteria, balloon catheter assemblies typically have a stiff proximal end and a more flexible distal end. If a hypotube is used at the proximal section, it is typically manufactured from a metallic material, such as stainless steel. The balloon catheter or the distal section of the assembly is typically manufactured from a more flexible, polymer product. Thus, the hypotube is relatively stiff, enabling the assembly to have good pushability while the balloon catheter or tube is more flexible, enabling the assembly to have sufficient trackability.

One problem associated with connecting a relatively stiff tubular member, such as a hypotube, to a more flexible tubular member, such as the catheter, is that the transition between the stiff hypotube and the more flexible catheter can result in kinking which can close the lumen of the hypotube or the lumen of the catheter thereby blocking flow through these lumens to the balloon.

To solve this problem, stiffening members have been provided which help serve as a transition member between the hypotube and the catheter. Such stiffening members are disclosed in U.S. Pat. Nos. 5,658,251 and 6,066,114.

As angioplasty and stent delivery procedures continue to increase, there is a continuing need to provide new catheter systems and improved trackability and flexibility.

SUMMARY OF THE DISCLOSURE

An improved hypotube for an intravenous device is disclosed which comprises a tubular shaft comprising a tubular wall defining a lumen and a main section connected to the distal section. The distal section of the tubular shaft comprises a first section connected to a second section. The first section is connected to the main section and disposed between the main section and the second section. The first section comprises at least one slit extending at least partially through the tubular wall for increasing the flexibility of the first section. In one embodiment, the second section comprises an elongated cut-out of the tubular wall to form an elongated stinger formed by a remaining portion of the tubular wall. The second section is more flexible than the first section. As a result, a transition is provided by the distal section of the hypotube which can be received in a balloon catheter lumen to thereby provide an enhanced transition in terms of both pushability and trackability between the hypotube and the balloon catheter.

In an alternative embodiment of the disclosed hypotube, the at least one slit of the first section is further characterized as being a spiral cut extending substantially along the first section. The spiral cut may have a constant or variable pitch and may extend through or partially through the tubular wall.

In another alternative embodiment, the second section of the distal section of the hypotube also comprises at least one slit for increasing the flexibility of the second section.

In yet another alternative embodiment, the distal section of the hypotube further comprises a middle section disposed between and connected to the first and second sections. The middle section comprises a plurality of slits in the tubular wall thereof to make the middle section less flexible than the second section but more flexible than the first section. In a further related alternative embodiment, at least a portion of the tubular wall of the middle section is partially collapsed.

In another embodiment, the middle section as described above includes a plurality of perforations as opposed to slits in the tubular wall thereof to make the middle section less flexible than the second section but more flexible than the first section. Again, in a further alternative embodiment, at least a portion of the tubular wall is partially collapsed. In still a further alternative embodiment, the middle section can comprise a slit and the perforated tubular wall disposed of this concept between the slit and the first section can be at least partially collapsed.

In any of the embodiments discussed herein, the stinger may be tapered and the distal section may be integrally connected to the main section or connected thereto by welding, adhesive or other attachment means. Further, the first and second sections may be integrally connected together or connected together by welding, adhesive or some other attachment means.

The hypotubes as described above all may be incorporated into an improved balloon catheter apparatus for angioplasty stent delivery system, etc.

In a further alternative embodiment, a method for fabricating hypotubes as described above is disclosed which comprises providing a tubular shaft comprising a tubular wall defining a lumen and a main section connected to a distal section, cutting a first section of the distal section that is disposed between and connected to the main section and a second section to provide at least one slit extending at least partially through the tubular wall of the first section for increasing the flexibility of the first section, and cutting the second section to provide an elongated cut-out of the tubular wall and an elongated stinger formed by a remaining portion of the tubular wall of the second section to increase flexibility of the second section and to make the second section more flexible than the first section.

In an alternative embodiment of the above method, the cutting, as described above, can be performed using a laser, such as a gas or solid state laser.

BRIEF DESCRIPTION OF THE DRAWINGS

The disclosed devices and methods are described more or less diagrammatically in the accompanying drawings wherein:

FIG. 1 is a partial side plan view of a disclosed hypotube as received in a balloon catheter shown in section;

FIG. 2 is a partial top plan view of the hypotube shown in FIG. 1;

FIG. 3 is a partial side plan view of another disclosed hypotube as received in a balloon catheter, shown in section;

FIG. 4 is an end view of the hypotube shown in FIG. 3;

FIG. 5 is an top plan view of the hypotube shown in FIG. 3;

FIG. 6 is a side plan view of another disclosed hypotube;

FIG. 7 is a side plan view of yet another disclosed hypotube;

FIG. 8 is an end view of the hypotube shown in FIG. 7;

FIG. 9 is a side plan view of yet another disclosed hypotube;

FIG. 10 is a side plan view of yet another disclosed hypotube;

FIG. 11 is a partial sectional view of a balloon catheter assembly incorporating another disclosed hypotube;

FIG. 12 is a partial perspective view of yet another disclosed hypotube;

FIG. 13 is a partial perspective view of yet another disclosed hypotube;

FIG. 14 is a partial perspective view of yet another disclosed hypotube;

FIG. 15 is a partial perspective view of yet another disclosed hypotube;

FIG. 16 is a partial perspective view of yet another disclosed hypotube; and

FIG. 17 is a partial perspective view of yet another disclosed hypotube.

Although the above-identified figures set forth a number of disclosed embodiments, other variations thereof are also contemplated. It should be understood that numerous modifications and other alternative embodiments can be devised by those skilled which will fall within the scope and spirit of this disclosure and the appended claims.

DETAILED DESCRIPTION OF THE ILLUSTRATED EMBODIMENTS

One embodiment of an improved hypotube 30 is disclosed in FIG. 1 whereby the hypotube 30 includes a tubular shaft having a main section 31 connected to a distal section 32. The distal section 32 can be divided into a first section 33 and a second section 34. The first section 33 is integrally connected to the main section 31 and, to increase the flexibility of the first section 33, one or more of slits or cuts is provided in the first section 33. To further improve the function of the distal section 32 as a transition element, the second section 34 includes a cut-out portion 36 whereby the tubular wall is cut away leaving a stinger that is partially shown at 37 in FIGS. 1 and 2. The stinger can also be tapered. The distal section 32 of the hypotube 30 is received in a catheter 38. Thus, the distal section 32 includes at least two distinct sections 33, 34, both with different flexibilities. The first section 33, by way of the slits or cuts 35 is more flexible than the main section 31 of the hypotube 30 but is less flexible than the second section 34 or stinger 37.

The catheter 38 may be a balloon catheter (see FIG. 11), a stent delivery catheter or part of another intravascular device. Further, a plurality of stingers 37 may be provided such as two, three, four stingers or more. Still further, the number or frequency of the slits or cuts 35 can be varied depending upon the flexibility or stiffness required. Also, it will be noted that the slits or cuts 35 may extend all the way through the tubular wall of the hypotube 30 or may only extend partially through the tubular wall of the hypotube 30.

As shown in FIGS. 3-13, a number of variations of the general concepts discussed above with respect to FIGS. 1 and 2 are available.

Specifically, turning to FIGS. 3-5, the hypotube 30a includes a main section 31a connected to a distal section 32a. The first section 33a of the distal section 32a includes a spiral cut or slit 35a as opposed to a single or a plurality of slits 35 as shown in FIGS. 1 and 2. Again, the second section 34a of the distal section 32a of the hypotube 30a includes a stinger 37a which is created by removing a portion of the tubular wall of the hypotube 30a to form a cut-out section 36a. The pitch of the spiral cut or slit 35a may be constant or may be varied throughout the first section 33a. Generally speaking with respect to spiral slits or cuts, see, e.g., FIGS. 7-11 and 13, the pitch of any spiral cut or slit used in an embodiment of the present invention may be constant or varied depending upon the stiffness transition characteristics desired. For example, the pitch may be increased for more flexibility or decreased for less flexibility. Further, the slit or cut may extend partially through or all the way through the tubular wall.

Turning to FIGS. 6-8, alternative hypotubes 30b are shown. Referring to FIG. 6, a hypotube is disclosed wherein the distal section 32b includes three distinct sections including a first section 33b, a second section 34b, but with a middle section 41b disposed therebetween. Similar to the hypotube 30a illustrated in FIGS. 3-5, the first section 33b of the hypotube 30b includes a single spiral cut 35b. The first section 32b is connected to a middle section 41b which, in turn, is connected to the stinger 37b. The middle section 41b includes a plurality of perforations 42b. The perforations are sufficient in number to make the middle section 41b more flexible than the first section 33b, but less flexible than the stinger 37b of the second section 34b. A cut 43b may be provided between the sections 33b and 41b for additional flexibility. By providing three distinct sections 33b, 41b and 34b, an improved transition in terms of flexibility is provided.

In a variation of the embodiment shown in FIG. 6, the hypotube 30c as shown in FIG. 7 includes a middle section 41c that has been collapsed as also shown in FIGS. 1 and 8. A cut 43b may be made in the middle section 41b as shown in FIG. 6. The cut 43b enables the perforated section 41b to be collapsed or pushed down to assume the position shown in FIG. 7. As shown in FIG. 8, even in the collapsed position, a sufficient cross section of the hypotube 30c is available for fluid flow to the balloon (not shown).

Turning to FIGS. 9 and 10, embodiments similar to those shown at 30b and 30c in FIGS. 6 and 7-8, respectively, are illustrated. In FIG. 9, a hypotube 30d is illustrated whereby the middle section 41d includes a plurality of cuts or slits 44d. In FIG. 10, a hypotube 30e is illustrated which includes a middle section 41e that is collapsed, similar to that shown for the hypotube 30c in FIGS. 7-8.

The advantageous hypotubes disclosed herein can be incorporated into known catheter systems including catheters for balloon angioplasty, and balloon expandable and self expanding stent delivery systems.

FIG. 11 illustrates a catheter apparatus 50 which includes a balloon catheter 51 connected at a proximal end to a manifold 52 and at a distal end to a balloon 53. The catheter 51 is configured to provide for a wire entry port 54 and a guidewire lumen 55. A transitioning hypotube 56 is provided inside the catheter 51. The hypotube 56 has a stepped configuration and includes a spiral cut 57. In the embodiment shown in FIG. 11, the spiral cut 57 has a varying pitch which increases in frequency towards the distal end 58 of the hypotube 56.

FIG. 12 illustrates a distal end 32f that features a compressed section 61 that forms a stinger. The compressed section 61 also includes a plurality of slits in a criss-cross pattern to increase the flexibility of the section 61. Similarly, referring to FIG. 13, a hypotube 30g is illustrated with a distal end section 32g that also features a compressed section 62 with horizontal cuts in the compressed section 62.

FIG. 14 illustrates a hypotube 30i that includes a distal end 32i with a compressed section 65 and a truncated end 66. The end 66 is rounded in the illustrated embodiment. FIG. 15 illustrates a hypotube 30j having a distal end section 32j that includes two stingers 67, 68. The stinger 67 is part of a compressed section with horizontal slits shown at 69. FIG. 16 illustrates a variation of FIG. 14 wherein a hypotube 30k includes a distal end section 32k having a compressed section 71 and a stinger 72 attached to the truncated end 73 of the compressed section 71. In FIG. 17, a further variation is presented in the form of a hypotube 30l that includes a distal end section 32l having a compressed section 75 with a truncated end 76 that is connected to two stingers 77, 78. The compressed section 75 includes a plurality of horizontal slits shown at 79.

The length of the distal sections 32, first section 33, second section 34 and middle section 41 (if included) may vary. For example, the length of the distal section 32 of the hypotube may range from about 7.6 cm to about 22.9 cm. The length of the first section 33 of the hypotube 30 may range from about 2.5 cm to about 15.2 cm. The length of the second section 34 of the hypotube 30 may range from about 2.5 cm to about 15.2 cm. Further, the length of the middle section 41 may range from about 2.5 cm to about 10.2 cm. While the illustrated embodiments indicate a preference for the first and second sections 33, 34 or first, middle and second sections 33, 41, 34 being integrally connected, it will be noted that these sections may comprise separate members that are connected to the distal end of the hypotube 30. The connection may be made by welding, adhesive or other suitable attachment means. The distal section 32 may be an integral member or may comprise separate sectional members 33, 34 or 33, 41, 34 that are connected together by welding, adhesive or other suitable attachment means.

The hypotubes are preferably formed from a conventional stainless steel, nitinol or other metallic material as well as plastic such as PEEK, polyimide, polycarbonate, etc. The changes in geometry of the distal ends 32 of the disclosed hypotube are preferably made with the use of a laser, either a gaseous laser or a solid state laser. Preferred lasers are $CO_2$ and YAG lasers.

Although specific embodiments and methods have been described, workers skilled in the art will realize that changes may be made in form and detail without departing from the spirit and scope of this disclosure.

What is claimed:

1. A catheter apparatus comprising:
a distal tubular member defining a first lumen,
and a proximal hypotube comprising a tubular shaft comprising a tubular wall defining a second lumen and a main section integrally connected to a distal section,
the distal section comprising a first section integrally connected to a second section, the first section being integrally connected to the main section and disposed between the main section and the second section,
the first section comprising at least one slit extending through the tubular wall, the at least one slit extending at least partially and circumferentially around the tubular wall, the at least one slit having a traverse length greater than a longitudinal length, the second section comprising a non-tubular stinger, the second section comprises an elongated axially extending cut out through the tubular wall and the stinger is formed from a remaining portion of the tubular wall,
a balloon,
the at least one slit being disposed in close proximity to the stinger,
the distal tubular member connected to the proximal hypotube such that the first and second lumens fluidly connected to form an inflation lumen, and
the balloon fluidly coupled to the inflation lumen,
the stinger extending distally from the distal end of the hypotube into the distal tubular member.

2. The catheter apparatus of claim 1 wherein the catheter apparatus is a stent delivery system.

3. The catheter apparatus of claim 2 wherein a distal end of the catheter is connected to a balloon.

4. The catheter apparatus of claim 2 wherein the catheter apparatus is a stent delivery system having a stent mounted to a balloon.

5. The catheter apparatus of claim 1 wherein the second section comprises at least one slit for increasing flexibility of the second section.

6. The catheter apparatus of claim 1 wherein the distal section further comprises a middle section disposed between and integrally connected to the first and second sections, the middle section being less flexible than the second section but more flexible than the first section.

7. The catheter apparatus of claim 6 wherein the middle section comprises a plurality of slits extending at least partially through the tubular wall thereof.

8. The catheter apparatus of claim 6 wherein the tubular wall of the middle section is at least partially collapsed.

9. The catheter apparatus of claim 1 wherein the distal section further comprises a middle section disposed between and integrally connected to the first and second sections, the middle section comprising a plurality of perforations in the tubular wall thereof to make the middle section less flexible than the second section but more flexible than the first section.

10. The catheter apparatus of claim 9 wherein the tubular wall of the middle section is at least partially collapsed.

11. The catheter apparatus of claim 9 wherein the middle section further comprises at least one slit through the tubular wall.

12. The catheter apparatus of claim 11 wherein the tubular wall of the middle section is at least partially collapsed between the slit and the second section.

13. The catheter apparatus of claim 1 wherein the stinger is tapered.

14. The catheter apparatus of claim 1 wherein the second section comprises a plurality of non-tubular stingers.

15. A catheter apparatus comprising:
   a distal tubular member defining a first lumen,
   and a proximal hypotube comprising a tubular shaft comprising a tubular wall defining a second lumen and a main section integrally connected to a distal section.
   the distal section comprising a first section integrally connected to a second section, the first section being integrally connected to the main section and disposed between the main section and the second section,
   the first section comprising at least one slit extending through the tubular wall, the at least one slit extending at least partially and circumferentially around the tubular wall, the at least one slit having a traverse length greater than a longitudinal length, the second section comprising a non-tubular stinger, wherein the stinger extending distally into the first lumen and being attached to the distal tubular member,
   a balloon
   the at least one slit being disposed in close proximity to the stinger,
   the distal tubular member connected to the proximal hypotube such that the first and second lumens fluidly connected to form an inflation lumen, and
   the balloon fluidly coupled to the inflation lumen,
   the stinger extending distally from the distal end of the hypotube into the distal tubular member.

16. A catheter apparatus comprising:
   a distal tubular member defining a first lumen,
   and a proximal hypotube comprising a tubular shaft comprising a tubular wall defining a second lumen and a main section integrally connected to a distal section,
   the distal section comprising a first section integrally connected to a second section, the first section being integrally connected to the main section and disposed between the main section and the second section,
   the first section comprising at least one slit extending through the tubular wall, the at least one slit extending at least partially and circumferentially around the tubular wall, the at least one slit having a traverse length greater than a longitudinal length,
   the second section comprising a non-tubular stinger, wherein the stinger is formed by a portion of the tubular wall,
   the at least one slit being disposed in close proximity to the stinger,
   the distal tubular member connected to the proximal hypotube such that the first and second lumens fluidly connected to form an inflation lumen, and
   the balloon fluidly coupled to the inflation lumen,
   the stinger extending distally from the distal end of the hypotube into the distal tubular member.

* * * * *